(12) United States Patent
Maclennan et al.

(10) Patent No.: US 8,158,396 B2
(45) Date of Patent: Apr. 17, 2012

(54) ETHANOL FERMENTATION PROCESS AND PRODUCTS

(75) Inventors: David Graham Maclennan, Killcare (AU); Mary Elizabeth Maclennan, Killcare (AU)

(73) Assignee: Alternative Fuels Corporation Pty Ltd, New South Wales (AU)

( * ) Notice: Subject to any disclaimer, the term of this patent is extended or adjusted under 35 U.S.C. 154(b) by 841 days.

(21) Appl. No.: 12/089,009

(22) PCT Filed: Oct. 3, 2006

(86) PCT No.: PCT/AU2006/001441
§ 371 (c)(1),
(2), (4) Date: Jul. 29, 2008

(87) PCT Pub. No.: WO2007/038833
PCT Pub. Date: Apr. 12, 2007

(65) Prior Publication Data
US 2008/0299630 A1 Dec. 4, 2008

(30) Foreign Application Priority Data
Oct. 3, 2005 (AU) ................. 2005905444

(51) Int. Cl.
*C12P 7/06* (2006.01)
*C12N 1/12* (2006.01)
*C12N 1/16* (2006.01)

(52) U.S. Cl. .......... 435/161; 435/255.1; 435/255.2; 435/255.4

(58) Field of Classification Search ............ 435/161, 435/255.1, 255.2, 255.4
See application file for complete search history.

(56) References Cited

U.S. PATENT DOCUMENTS

| 4,310,629 A | 1/1982 | Muller et al. |
| 4,346,113 A | 8/1982 | Faust et al. |

FOREIGN PATENT DOCUMENTS

WO 85/02864 A 7/1985

OTHER PUBLICATIONS

Furusaki et al "Rotary Reactor Producing Ethanol with Immobilized Yeast Cells" (1985) vol. 38 No. 1 pp. 1-7.*

* cited by examiner

*Primary Examiner* — Herbert J Lilling
(74) *Attorney, Agent, or Firm* — The Webb Law Firm

(57) ABSTRACT

The present invention provides a novel process for ethanol fermentation which uses a high concentration of fresh yeast to co produce ethanol and good quality yeast.

13 Claims, No Drawings

ETHANOL FERMENTATION PROCESS AND PRODUCTS

CROSS-REFERENCE TO RELATED APPLICATIONS

The present application claims priority from Australian Provisional Patent Application No 2005905444 filed on 3 Oct. 2005, the content of which is incorporated herein by reference.

FIELD OF THE INVENTION

The present invention is in the field of ethanol production which involves anaerobic fermentation of sugars by yeast to produce ethanol and yeast and yeast derived products for human consumption.

BACKGROUND OF THE INVENTION

Beer, wine and spirituous liquor, as well as other lesser known alcoholic beverages, are the fermentation products of yeasts such as *Saccharomyces cerevisiae* or in the case of beers, usually *S. carlsburgiensis*. Yeasts are unicellular fungi that reproduce asexually by budding or fission and the reaction by which alcoholic beverages are produced is generally referred to as "fermentation" and may be summarized as: Yeast+Glucose→Alcohol (Ethanol)+$CO_2$, wherein the production of alcohol occurs best in the absence of oxygen.

For the yeast, both the alcohol and carbon dioxide are waste products, and as the yeast continues to grow and metabolize in the sugar solution the accumulation of alcohol becomes increasingly toxic such that when the yeast is exposed to a high concentration of yeast (e.g. 12-18% v/v) for an extended period of time the yeast cells are lysed and ultimately killed. The extended exposure of yeast to such high concentrations of ethanol reduces the yeast extract yield and the yeast recovered is usually only recovered for low value ruminant animal feed.

The alcohol concentration in beer is considerably lower than wine (9-15% v/v) and is typically about 5% v/v. Once the beer has reached its optimum alcohol level the yeast can be recycled and used again until it eventually dies or, alternatively, small amounts of yeast can be recovered if they are in relatively good condition. To be useful as a food grade product, the recovered yeast is usually de-bittered to remove hop-derived flavours.

In the past 50 years increasing attention has been focussed on production of fuel grade ethanol. The emphasis in production of fuel ethanol is to maximise efficiency of ethanol production. This is normally achieved by providing the minimum amount of yeast necessary to effect the efficient and rapid conversion of sugar to ethanol. Often the yeast is partially recycled from the end of the fermentation process so that it can be re-used for as long as possible. The yeast at the end of the process is of poor nutritional value, and is normally recovered together with any non-fermentable material in the medium, and used for ruminant animal feed.

The production of yeast for human food consumption, such as for example, in the baking industry, or for further processing to a range of products used as flavours or flavour enhancers, involves aerobic fermentation. Yeast for such purposes is most efficiently produced with minimum production of ethanol or other by-products.

SUMMARY OF THE INVENTION

The inventors sought to provide a single process to co-produce ethanol at high concentrations and yeast in good condition. Most preferably the yeast recovered after the process is high quality food grade yeast. To that end, the present invention provides a novel process for ethanol fermentation which uses a high concentration of fresh yeast to co produce ethanol and good quality yeast.

In a first aspect the present invention provides a novel process for co-producing ethanol and yeast cells in good physical and physiological condition comprising:
(a) providing fresh yeast cells that can ferment sugar under suitable conditions;
(b) providing a ferment medium that is substantially free of particulate matter and which comprises a fermentable sugar;
(c) combining the fresh yeast cells and ferment medium at a concentration of 5-60 yeast cells g/L and incubating the fresh yeast cells in the ferment medium for a time and under conditions suitable for the yeast cells to effect conversion of the fermentable sugar to ethanol;
(d) continuing the incubation until a desired concentration of ethanol is produced, and one or more yeast cells are in good physical and physiological condition.

Preferably the process further comprises recovering the ethanol; and preferably the process comprises recovering one or more yeast cells from the ferment medium in good physical and physiological condition.

Preferably the yeast cells are *Saccharomyces*, *Candida* or *Torula* species or a mixture thereof. In one preferred embodiment the yeast cells are *Saccharomyces cerevisiae* or *Saccharomyces bayanus* or a mixture thereof.

Preferably the fresh yeast cells are a culture of yeast cells, It will be appreciated by the person skilled in the art that a culture of yeast cells which comprises many cells is not totally homogeneous. Similarly the recovered yeast cells are not expected to be totally homogeneous.

As used herein the term "fresh" refers to being in good physical and physiological condition and does not include yeast cells that are recycled from a previous anaerobic fermentation step or process. Accordingly, cells that have already been used in a fermentation process are not suitable for use in step (a) of the present invention. Preferably a fresh yeast cell is one which is grown fully aerobically with no nutritional or environmental limitations.

The term "physical" condition refers to the condition of a cell as a whole including the cell wall and cell constituents. A yeast cell that is in good physical condition has its cell wall intact and allows substantially no leakage of cell constituents from the cell. The crude protein content of a yeast cell in good condition is preferably about 45-50% dry matter (expressed as total N×6.25), but can range from 35-60% depending on the yeast strain. This terminology can also be used to described a yeast culture.

The term good "physiological" condition refers to a yeast cell that is capable of growth and reproduction. This can be ascertained by subculturing the yeast onto fresh medium.

Preferably the yeast cell concentration in the ferment medium is in the range of about 9-40 g/l, or 10-40 g/L, or 15-35 g/L, more preferably 15-25 g/L. The yeast cell concentration is expressed as the dry weight of the yeast.

In one embodiment of the invention the amount of the fermentable sugar in the ferment medium when combined with the fresh yeast is 100-300 g/L, more preferably, 120-260 g/L, more preferably 130-240 g/L.

The conditions of the ferment medium are modified according to the needs of a particular yeast strain and it is within the scope of the present invention to modify the constituents of the medium to optimise the conditions.

In one preferred embodiment, the pH of the ferment medium is in the range 2.5-6.5, more preferably the pH is in the range 3.0-5.0, and most preferably the pH is in the range 3.0-3.6.

Preferably the concentration of dissolved oxygen in the ferment medium is below 500 ppb, more preferably below 250 ppb, and most preferably less than 50 ppb. These oxygen conditions for fermentation are considered by those skilled in the art to be anaerobic conditions.

In another preferred embodiment the fermentation incubation is performed at a temperature range of about 20-45° C., more preferably 25-35° C. and most preferably 30-35° C.

Preferably the yeast is incubated in the medium for 10-50 hours, more preferably 15-30 hours. It is understood that the time for incubation is dependent on the amount of ethanol produced and the continued good condition of the yeast. Preferably the concentration of the ethanol produced is 8-18% v/v, more preferably 12-14% v/v.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DETAILED DESCRIPTION OF THE INVENTION

Providing a Yeast

According to the present invention in step (a) fresh yeast cells are provided. In one embodiment of the invention step (a) further comprises growing a culture of fresh yeast cells. To that end the present process involves selecting a strain of yeast that is suitable for producing ethanol and which is most preferably approved for use as a food by the appropriate food authority such as for example Food Standards Australia and New Zealand (FSANZ) or US Food and Drug Administration (FDA).

Yeasts that are known to be acceptable for food consumption include for example *Saccharomyces*, *Candida* or *Torula* species. Preferably, according to the present invention the yeast is tolerant of high ethanol concentrations. Other preferred characteristics of a yeast which are well known in the art include high tolerance to low pH substrates, high temperature tolerance and auto-flocculent properties. Most preferably the yeast is *Saccharomyces cerevisiae* or *Saccharomyces bayanus* or a mixture of both.

Growing the yeast cells further involves providing a growth medium which contains a fermentable sugar, together with macro and micro nutrients necessary for the optimum growth of yeast under aerobic conditions. The yeast is grown for a time and under conditions that are optimum for the selected yeast.

The growth medium is preferably substantially free of particulate or insoluble matter (e.g. fibre) and this can be achieved by subjecting the medium to conventional separation means such as by settling, centrifugation, or filtration to separate any particulate matter.

Accordingly in one embodiment of the invention step (a) comprises subjecting a growth medium comprising a fermentable sugar to a separation step to separate any particulate matter and provide a medium that is substantially free of particulate matter.

Preferably the growth medium is sterilised. The yeast to be grown is most preferably for a food product, and preferably therefore the growth of the yeast is carried out under aseptic conditions and in accordance with known human food processing regulations (e.g. cleanliness, additives, processing aids, etc) as defined in the laws and regulations of the country involved, for example standards such as Food Standards Australia and New Zealand (FSANZ) or US Food and Drug Administration (FDA).

The fermentable sugar is derived from any material which can be processed to provide a fermentable sugar, such as grains, corn, starchy tubers, sugar cane or beet, cellulosic materials, or fruit. Fermentable sugars include for example glucose, sucrose, fructose and lactose.

The fermentable sugar can be provided in a form that is ready to use or it can be prepared as a part of the process described herein. The fermentable sugar can be provided independently of or together with a complete growth medium.

Various processes for preparing a fermentable sugar substrate for a yeast growth medium are known by the person skilled the art. For example in one embodiment, to convert starch to sugars in a starch containing grain product, grains are suspended in water and partially hydrolysed and liquefied with an enzyme to convert the starch content of the grains to dextrins. In one method for providing a fermentable sugar a dextrin product is saccharified with another enzyme to complete the conversion of the starch into glucose. Other methods for obtaining a fermentable sugar are known and are within the scope of the invention.

Preferably the growth medium comprises 10-120 gm/liter of fermentable sugar, more preferably 20-80 gm/liter fermentable sugar, more preferably 30-50 gm/liter fermentable sugar.

Macro and micro nutrients include, for example, a utilisable nitrogen source, phosphorus, potassium, magnesium, calcium, sulphur and other minerals, minor trace elements and vitamins. Their optimum concentration will be defined by the yeast to be used. The person skilled in the art will be familiar with the need to optimise the concentration of macro and micro nutrients depending on the use of a specific yeast. The substrate and all equipment are preferably sterilised prior to use so as to exclude contamination by any other organisms.

The culture conditions are controlled with respect to the concentration of dissolved oxygen, pH, and temperature such as to maximise cell production and minimise production of by-products, for example ethanol, glycerol, etc. The concentration of dissolved oxygen is controlled at a level that ensures fully oxidative metabolism of the yeast. Oxygen may be supplied by air or gaseous oxygen, which is vigorously distributed through the substrate so as to maintain the required dissolved oxygen level.

Other conditions such as pH can be controlled for example by the addition of a suitable food grade control agent such as for example a mineral or organic acid, or alkali, or $NH_4OH$. In one embodiment the pH is in the range 2.5-6.5, more preferably the pH is in the range 3.0-5.0, and most preferably the pH is in the range 3.0-3.6.

The optimum temperature for the growth of many yeast strains is normally in the range of about 20-45° C., more preferably 25-35° C. and most preferably 30-35° C. The person skilled in the art is aware that this condition is yeast strain specific and can be optimised through experimentation.

Dissolved oxygen concentration in the medium is preferably maintained above 1600 ppb $O_2$ using injected air or $O_2$ with vigorous mixing of the medium. It is also possible to achieve satisfactory aerobic growth of some suitable yeast strains at dissolved oxygen concentrations below 1600 ppb $O_2$, even down to 50 ppb $O_2$, although seldom less than about 250 ppb $O_2$.

According to the invention, the fresh yeast cell population is preferably grown relatively rapidly. The fresh yeast cell culture can be grown in a batch culture, or in a preferred embodiment, as a continuous culture to which growth medium is added at a pre-determined rate while grown yeast culture is removed at the same rate. In a preferred embodiment of the present invention after a period of time of yeast cell growth, fresh sterilised medium is added continuously to the culture at a constant rate to achieve a dilution in the range of 0.05-0.35 fermenter volumes/hour ($hr^{-1}$) more preferably 0.10-0.25 $hr^{-1}$. Preferably after about 2-10 volumes of fresh growth medium have been added the yeast concentration is suitably high enough.

Preferably, a concentration of fresh yeast of about 5-60 gm/liter is grown. More preferably the fresh yeast cell concentration reaches a steady state concentration of 10-40 gm/liter, and more preferably 15-25 gm/liter, depending on the concentration of the sugar substrate in the growth medium and the yeast strain selected.

If the yeast concentration in the out flowing culture is not as desired for the second stage, the culture can be diluted or yeast concentration can be increased (e.g. by centrifugation or settling) to the desired yeast concentration.

Fermentation

According to the present invention in step (b) a ferment medium is provided that is substantially free of particulate matter and comprises a fermentable sugar.

In step (c) fresh yeast cells (which are optionally grown as part of step (a)) are incubated in the ferment medium at a yeast concentration of 5-60 g/L for a time and under conditions suitable for the yeast cells to effect conversion of the sugar substrate to ethanol and $CO_2$. In a preferred embodiment the concentration of yeast cells in the ferment medium is 10-40 gm/liter, and more preferably 15-25 gm/liter.

The ferment medium comprises sugar-containing substrate and other nutrients in amounts that are sufficient to maintain the number of yeast cells but not increase the cell population.

In a preferred embodiment of the invention the ferment medium comprising fermentable sugar is incubated with the culture of fresh yeast cells such that the total amount of fermentable sugar is equivalent to approximately twice the weight concentration of the desired ethanol to be produced. For example if the desired ethanol concentration to be produced in the final culture after anaerobic fermentation is 100 g/liter (equivalent to 12.6% v/v ethanol), then the amount of fermentable sugar in the ferment medium to be added to the fresh yeast cell culture is approximately 200 gm/liter.

Preferably the fermentable sugar concentration in the ferment medium when combined with fresh yeast cells prior to conversion to ethanol is up to about 300 gm/liter depending on which yeast strain is selected and the conditions used for both the aerobic growth and anaerobic fermentation. More preferably the concentration of fermentable sugar is in the range 130 to 240 gm/liter. The ferment medium or any components thereof may be added to the fresh yeast, or the fresh yeast may be added to the ferment medium. Addition can be as a single addition, continuously, or incrementally.

The ferment medium also comprises nutrients preferably of the type defined above for the growth of the yeast cells. The type and amount of nutrients required is dependent upon the selected yeast strain and its optimum production of ethanol. It is within the scope of the invention to optimise the nutrients. Furthermore it is within the scope of the invention to optimise the conditions such as pH and temperature. The pH and temperature conditions for the fermentation step are expected to be similar to or the same as for the growth of the yeast.

By contrast, air or gaseous oxygen is supplied and dissolved oxygen is controlled at a minimum level sufficient to provide the minimum oxidative requirements for maintenance of the yeast and to allow substantially anaerobic conversion of the sugar to alcohol at a rapid rate.

In one embodiment, the conditions of fermentation comprise a dissolved $O_2$ level below 500 ppb or, more preferably and depending on yeast strain selected, less than 250 bp more preferably less than 50 ppb. Within the context of the invention, these conditions are considered to be suitable for anaerobic fermentation.

Fermentation is carried out under anaerobic conditions in one or more anaerobic fermenting means (e.g. a vessel). In one embodiment yeast cells are incubated in a vessel and the conditions of the vessel can be controlled to achieve optimal fermentation.

The process can be a continuous, semi-continuous or batch culture process. Also, the ferment medium comprising the fermentable sugar and any required nutrients can be provided in the process in a continuous, semi-continuous, batch wise, or incremental way. The culture of fresh yeast cells in the anaerobic fermentation can be mixed (e.g. by mixing agitation) or static Fermentation is allowed to proceed until the ethanol concentration reaches a desired level. At this stage the product preferably comprises a mixture of ethanol at a concentration of at least about 8% v/v and a yeast in good physical and physiological condition.

Preferably the ethanol content reaches about 8-18%, more preferably 8-16% v/v, more preferably 10-16% v/v, and most preferably 12-14% v/v.

The yeast cells are removed from their exposure to ethanol before the ethanol reaches a concentration that is detrimental to the condition of the yeast. This can be determined experimentally for example by measuring the crude protein content of an aliquot of yeast cells separated from the whole culture and washed to remove adhering medium components.

Yeast and Ethanol Recovery

The yeast can be recovered from the ferment medium using conventional separation techniques such as settling or more preferably centrifugation. The means of separating the yeast from the ferment medium after fermentation but before distillation or other processing, preferably minimises damage to the yeast and prevents loss of ethanol during yeast recovery.

In one embodiment the recovered yeast is washed in an aqueous solution such as water to remove any undesirable material from the recovered yeast. The recovered yeast is in good physical and physiological condition and preferably it has a protein content of about 35-65%, more preferably about 45-50% and most preferably 40-48%, expressed as Total N×6.25.

The recovered yeast can be used as a food ingredient without further processing.

In one embodiment the yeast recovered from the process is dried, for example as a savoury food ingredient.

In another embodiment, the recovered yeast is processed to produce yeast auto-lysates or lysates with or without removal of unlysed or partially lysed yeast cells. The yeast autolysate or lysate is useful for food ingredients. An auto-lysate or lysate is the product of autolysis or lysis respectively, including soluble and insoluble products. The principle soluble products are proteins, amino acids and polysaccharides or derivatives thereof and the principle non-soluble autolytic products are substantially non-degradable (by autolysis) polysaccharides.

The yeast may be further processed to provide yeast extract products such as peptides, peptones, nucleotides, amino acids, or specific yeast cell components such as protein fractions, which may themselves be processed to produce other food products with specific functional properties such as egg yolk/white substitutes.

The yeast preferably yields between 45-65% extract, preferably 50-65% extract, relative to the weight of yeast. Other products may be recovered such as cell walls and cell wall components such as chitin, glucans, mannans, oligosaccharides. Products may also have application in the pharmaceutical, aqua culture, animal feed and other industries The liquor can be distilled to recover the ethanol using standard techniques. From an ethanol production point of view, the higher the ethanol concentration achieved the better, as it minimises distillation costs. Preferably the present invention provides ethanol at a concentration of 8-18%, more preferably 8-16%, more preferably 10-14% and most preferably 12-14%. To provide a liquor with high ethanol concentration by distillation.

According to the present invention the ethanol concentration is preferably in the range of about 8-18%, more preferably 10-16%, more preferably 12-14%.

In one embodiment the yeast extract yield is up to about 65% and the ethanol concentration is about 8%. In another embodiment the yeast extract yield is up to about 45% and the ethanol concentration is about 14%.

Preferably, part or all of the process is to be carried out under hygienic conditions such that any of the products designated for human consumption will meet regulatory requirements for food quality products in Australia and other countries.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

In an example of the invention, a sterilised medium containing 10 gm per liter glucose, together with sources of nitrogen, phosphorus, potassium, magnesium, calcium, sulphur, trace elements and vitamins, was incubated together with an actively growing culture of a strain of *Saccharomyces cerevisiae* in a pre-sterilised chemostat vessel. The pH was automatically controlled at 3.6 by addition of $NH_4OH$, and the temperature controlled at 30° C. Dissolved oxygen was automatically controlled at 2000 ppb $O_2$ using injection $O_2$ with vigorous mixing.

After 10 hrs of batch growth, fresh sterilised medium containing 42 g glucose/liter with proportionately increased sources of the above nutrients was added continuously to the culture to achieve a dilution rate of 0.10 fermenter volumes per hour while maintaining a constant volume by overflow of the culture. After 30 hrs in continuous aerated culture a steady state was achieved at a yeast concentration of 19 g/liter and an ethanol concentration of <0.5% v/v. The overflowing yeast culture was collected in a stirred vessel controlled at 30° C.

Glucose concentrate (380 g glucose/liter) was added to the vessel at the same volumetric flow rate as the yeast culture, such that the combined inlet flows contained yeast and glucose at concentrations of 9.5 and 190 g/liter respectively. When the vessel was full it was shut off from air and maintained under anaerobic conditions (<50 ppb $O_2$) for 45 hrs. During this time the cell concentration rose to 10.5 g dry weight/liter due to $CO_2$ evolution and some anaerobic growth, and the ethanol concentration rose to 12.8% v/v.

The culture from the anaerobic fermentation was separated by centrifugation and the yeast re-suspended in water to a cell concentration of 170 g dry weight/liter. This was used for the preparation of yeast extract using known technology.

A yield of 47% (47 gm dry weight yeast extract per 100 gm dry weight of yeast processed was obtained from the anaerobic yeast which had been exposed to ethanol concentrations up to 12.8% v/v for periods up to 45 hours.

The product had a typical yeast extract savoury smell and flavour.

The invention claimed is:

1. A process for co-producing ethanol and yeast cells comprising:
   (a) providing a culture of fresh yeast cells that can produce ethanol from fermentable sugars under suitable conditions;
   (b) providing a ferment medium that is substantially free of particulate matter and which comprises a fermentable sugar;
   (c) combining the fresh yeast cells and ferment medium at a concentration of 5-60 yeast cells g/L and incubating the fresh yeast cells anaerobically in the ferment medium for a time and under conditions suitable for the yeast cells to effect conversion of the substrate to ethanol;
   (d) continuing the incubation until ethanol is produced in a concentration of 8-18% v/v, and the yeast cells in the ferment medium have a protein content of 35-65%; and
   (e) recovering the yeast cells in a manner such that their protein content is 35-65%.

2. The process according to claim 1 further comprising the step of:
   recovering the ethanol.

3. The process according to claim 1 wherein the yeast strain is *Saccharomyces, Torula* or *Candida*.

4. The process according to claim 1 wherein the yeast strain is *Saccharomyces cerevisiae* or *Saccharomyces bayanus* or a mixture thereof.

5. The process according to claim 1, wherein the yeast cell concentration in the ferment medium is in the range 10-40 g/L.

6. The process according to claim 1 wherein the concentration of the fermentable carbohydrate in the ferment medium is 5-300 g/L.

7. The process according to claim 1 wherein the pH of the ferment medium is in the range 2.5-6.5.

8. The process according to claim 1 wherein the temperature is about 20-45° C.

9. The process according to claim 1 wherein the yeast is incubated in the medium for 10-50 hours.

10. The process according to claim 1 wherein the concentration of the ethanol produced is 8-16% v/v.

11. The process according to claim 1 wherein the concentration of the ethanol produced is 10-16% v/v.

12. The process according to claim 1 wherein the concentration of the ethanol produced is 12-14% v/v.

13. The process according to claim 1 further comprising the step of processing the recovered yeast cells.

* * * * *